United States Patent
Jo (10) Patent No.: US 9,934,588 B2
(45) Date of Patent: Apr. 3, 2018

(54) METHOD OF AND APPARATUS FOR PROVIDING MEDICAL IMAGE

(71) Applicant: SAMSUNG ELECTRONICS CO., LTD., Suwon-si (KR)

(72) Inventor: Hyun-hee Jo, Osan-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/527,326

(22) Filed: Oct. 29, 2014

(65) Prior Publication Data
US 2015/0178925 A1    Jun. 25, 2015

(30) Foreign Application Priority Data
Dec. 23, 2013    (KR) .................. 10-2013-0161783

(51) Int. Cl.
| | |
|---|---|
| G06K 9/00 | (2006.01) |
| G06T 7/33 | (2017.01) |
| A61B 6/00 | (2006.01) |
| A61B 8/00 | (2006.01) |
| A61B 8/08 | (2006.01) |

(Continued)

(52) U.S. Cl.
CPC ............. *G06T 7/344* (2017.01); *A61B 5/055* (2013.01); *A61B 5/7425* (2013.01); *A61B 6/463* (2013.01); *A61B 6/502* (2013.01); *A61B 6/5235* (2013.01); *A61B 6/5247* (2013.01); *A61B 8/0825* (2013.01); *A61B 8/463* (2013.01); *A61B 8/5261* (2013.01); *G06F 3/04842* (2013.01); *G06F 19/321* (2013.01); *G06F 19/3437* (2013.01); *G06T 2207/10088* (2013.01); *G06T 2207/10104* (2013.01); *G06T 2207/10116* (2013.01); *G06T 2207/10132* (2013.01); *G06T 2207/30068* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 5,709,206 A | * | 1/1998 | Teboul ............... | A61B 8/0825 128/915 |
| 8,452,613 B2 | | 5/2013 | Meinel et al. | |

(Continued)

FOREIGN PATENT DOCUMENTS

| | | |
|---|---|---|
| JP | 2003-144412 A | 5/2003 |
| JP | 2009-077780 A | 4/2009 |
| KR | 10-2012-0111871 A | 10/2012 |

OTHER PUBLICATIONS

Communication dated Nov. 19, 2014 issued by Korean Intellectual Property Office in counterpart Korean Patent Application No. 10-2013-0161783.

(Continued)

*Primary Examiner* — Shervin Nakhjavan
(74) *Attorney, Agent, or Firm* — Sughrue Mion, PLLC (57) ABSTRACT

A method of providing multimodal medical images includes: loading first image data and second image data obtained by two different imaging modalities; generating object modeling data based on at least one of the first image data and the second image data; and displaying, on a display, the first image data, the second image data, and the object modeling data. The object modeling data is a virtual model of a body tissue of an object.

29 Claims, 5 Drawing Sheets

(51) Int. Cl.
*A61B 5/055* (2006.01)
*G06F 3/0484* (2013.01)
*A61B 5/00* (2006.01)
*G06F 19/00* (2018.01)

(56) References Cited

U.S. PATENT DOCUMENTS

| | | | |
|---|---|---|---|
| 8,989,842 B2* | 3/2015 | Li | A61B 5/06 128/916 |
| 2002/0156375 A1* | 10/2002 | Kessman | A61B 8/0841 600/439 |
| 2003/0233039 A1* | 12/2003 | Shao | G06T 7/0038 600/407 |
| 2004/0213443 A1* | 10/2004 | Haussecker | G01Q 30/04 382/128 |
| 2006/0078195 A1* | 4/2006 | Vaillant | A61B 6/032 382/154 |
| 2006/0079759 A1* | 4/2006 | Vaillant | A61B 34/20 600/424 |
| 2007/0010743 A1* | 1/2007 | Arai | A61B 8/13 600/443 |
| 2007/0081712 A1* | 4/2007 | Huang | G06T 7/0028 382/128 |
| 2008/0032325 A1* | 2/2008 | DiMarzio | G02B 21/0004 435/29 |
| 2008/0181470 A1* | 7/2008 | Camus | A61B 6/505 382/128 |
| 2008/0221425 A1* | 9/2008 | Olson | A61B 90/36 600/407 |
| 2008/0292164 A1 | 11/2008 | Azar et al. | |
| 2008/0297502 A1* | 12/2008 | Simard | G06T 7/0022 345/420 |
| 2009/0135191 A1* | 5/2009 | Azar | A61B 6/502 345/522 |
| 2009/0213034 A1* | 8/2009 | Wu | G06F 19/3406 345/1.1 |
| 2010/0067768 A1* | 3/2010 | Ionasec | G06K 9/621 382/131 |
| 2010/0156904 A1* | 6/2010 | Hartung | G06T 7/0085 345/420 |
| 2010/0198063 A1 | 8/2010 | Huber et al. | |
| 2010/0312096 A1* | 12/2010 | Guttman | A61B 5/418 600/411 |
| 2011/0125526 A1* | 5/2011 | Gustafson | G06F 19/321 705/3 |
| 2011/0157154 A1* | 6/2011 | Bernard | G06T 11/60 345/419 |
| 2011/0235884 A1* | 9/2011 | Schreibmann | G06T 7/0024 382/131 |
| 2012/0087563 A1* | 4/2012 | Ionasec | G06T 7/0032 382/131 |
| 2012/0172700 A1* | 7/2012 | Krishnan | A61B 6/032 600/407 |
| 2012/0249546 A1* | 10/2012 | Tschirren | G06T 19/00 345/419 |
| 2012/0253170 A1* | 10/2012 | Kim | A61B 34/10 600/410 |
| 2012/0253173 A1* | 10/2012 | Endo | G06T 11/008 600/411 |
| 2012/0262460 A1 | 10/2012 | Endo et al. | |
| 2013/0034203 A1* | 2/2013 | Wang | A61B 6/03 378/41 |
| 2013/0035583 A1* | 2/2013 | Park | A61B 6/032 600/411 |
| 2013/0090554 A1* | 4/2013 | Zvuloni | A61B 10/0241 600/424 |
| 2013/0129174 A1* | 5/2013 | Grbic | G06T 7/0012 382/131 |
| 2013/0211230 A1 | 8/2013 | Sperling | |
| 2013/0324841 A1* | 12/2013 | Kamen | A61B 8/0841 600/424 |
| 2014/0022250 A1* | 1/2014 | Mansi | G06T 19/20 345/420 |
| 2014/0029812 A1* | 1/2014 | Kriston | G06T 7/0028 382/128 |
| 2014/0037177 A1* | 2/2014 | Endo | G06T 7/0028 382/131 |
| 2014/0126789 A1* | 5/2014 | Ban | G06T 7/0024 382/128 |
| 2014/0323845 A1* | 10/2014 | Forsberg | A61B 5/4561 600/407 |
| 2015/0131880 A1* | 5/2015 | Wang | G06T 3/0075 382/131 |
| 2015/0302638 A1* | 10/2015 | Jago | A61B 8/0866 345/420 |

OTHER PUBLICATIONS

Extended Search Report dated Jun. 3, 2015, issued by the European Patent Office in counterpart European Patent Application No. 14193500.7.
Communication dated May 28, 2015, issued by the Korean Intellectual Property Office in counterpart Korean patent Application No. KR 10-2013-0161783.
Communication dated Aug. 4, 2015, issued by the Korean Intellectual Property Office in counterpart Korean patent Application No. KR 10-2013-0161783.
Di Carli, Marcelo F., et al., "Clinical Myocardial Perfusion PET/CT", The Journal of Nuclear Medicine, May 2007, vol. 48, No. 5, p. 783-793, XP055190987.
Quon, Andrew, et al. "Flying Through" and 'Flying Around' a PET/CT Scan: Pilot Study and Development of 3D Integrated 18F-FDG PET/CT for Virtual Bronchoscopy and Colonoscopy, The Journal of Nuclear Medicine, Jul. 2006, vol. 47, No. 7, p. 1081-1087, XP055190981.
Holz, Andrew, et al., 'Expanding the Versatility of Cardiac PET/CT; Feasibility of Delayed Contrast Enhancement CT for Infarct Detection in a Porcine Model, The Journal of Nuclear Medicine, Feb. 2009, vol. 50, No. 2, p. 259-265, XP055190999.
T. Hopp, et al., "Automatic multimodal 2D/3D breast image registration using biomechanical FEM models and intensity-based optimization", Medical Image Analysis, vol. 17, No. 2, Feb. 1, 2013, pp. 209-218.
Communication dated May 24, 2017, issued by the European Patent Office in counterpart European application No. 14 193 500.7.

* cited by examiner

METHOD OF AND APPARATUS FOR PROVIDING MEDICAL IMAGE

CROSS-REFERENCE TO RELATED APPLICATION

This application claims priority from Korean Patent Application No. 10-2013-0161783, filed on Dec. 23, 2013, in the Korean Intellectual Property Office, the disclosure of which is incorporated herein in its entirety by reference.

BACKGROUND

1. Field

Apparatuses and methods consistent with exemplary embodiments relate to a method of providing a variety of medical images and a medical imaging apparatus for providing the same.

2. Description of the Related Art

In order to scan an internal body structure of a patient, various medical imaging apparatuses such as ultrasound, a magnetic resonance imaging (MRI), computed tomography (CT), X-ray and/or positron emission tomography (PET) are used.

Medical images acquired by the above-listed medical imaging apparatuses have different features, and thus the acquired medical images include different representations of body tissues. Therefore, a user needs to compare various medical images to diagnose a condition of a patient. For example, in order to examine a patient's breast tissues, the user may review a mammographic image, an MR image, an ultrasound image, or other images captured by a medical imaging apparatus. When using a mammogram, the user may quickly scan the breast tissues of the patient. However, since the mammogram only provides two-dimensional (2D) images to the user, the user cannot view the depth of the tissues. In addition, since the user needs to apply pressure to the breast of the patient when scanning the breast tissues using the mammogram, the patient may experience pain. The ultrasonic imaging has lower sensitivity but higher specificity of tissues. On the other hand, an MRI has higher sensitivity but lower specificity of tissues. Therefore, medical images acquired by using, for example, the ultrasonic imaging and the MRI may be analyzed together to accurately diagnose a patient's condition.

However, each medical image has different features, and thus it may be difficult to compare the medical images. For example, in the case of the mammogram, a patient needs to stand while undergoing the mammogram during which pressure is applied to breast tissues of the patient. The patient lies supine while an MR image is acquired. Also, during ultrasonic imaging, the patient lies supine while an ultrasound image is acquired. The breast tissues include soft tissues, and thus, shapes thereof may change due to a posture of the patient, gravity, external pressure, etc. As a result, the medical images acquired by various medical imaging techniques may not be easily compared with each other or registered.

SUMMARY

Exemplary embodiments may address at least the above problems and/or disadvantages and other disadvantages not described above. The exemplary embodiments are not required to overcome the disadvantages described above, and may not overcome any of the problems described above.

One or more exemplary embodiments provide a medical imaging apparatus which allows a user to easily compare a multimodality image to another multimodality image.

One or more exemplary embodiments also provide a medical imaging apparatus which may extract medical information from medical images and provide medical information to a user to be easily used by the user.

According to an aspect of an exemplary embodiment, there is provided a method of providing medical information by a medical imaging apparatus, the method including: loading first image data and second image data; generating object modeling data based on information about shapes of body tissues of an object included in the first image data; and displaying the first image data, the second image data, and the revised object modeling data via an image viewer. The object modeling data is a virtual model embodying a body tissue structure of the object.

The method may further include, as at least one location is selected on the displayed object modeling data, indicating locations on the displayed first image data and the displayed second image data which correspond to the at least one selected location.

The indicating of the locations may include indicating a marker on at least one location on the first image data and a marker on at least one location on the second image data from among the locations on the first image data and the second image data corresponding to the at least one selected location.

The indicating of the locations may include: determining at least one area of a body tissue structure which is among areas of body tissue structures of the object modeling data and corresponds to the at least one selected location; and displaying an area on the displayed first image data and an area on the displayed second image data which correspond to the area of the at least one body tissue structure.

The method may further include generating diagnostic information necessary to diagnose a condition of a patient based on the object modeling data. The displaying the first image data, the second image data, and the object modeling data may include further displaying the diagnostic information by using the image viewer.

The object may be breast tissue, and the diagnostic information may include at least one of breast density, background parenchymal enhancement (BPE), degree of suspicion, and morpho-dynamic index (MDI).

The second image data may include an image, at least one of a point in time when an image is captured, modality of the image, a posture of a scanned object, and a protocol by which the image is captured that is different from a protocol by which an image included in the first image data is captured.

The displaying of the first image data, the second image data, and the object modeling data may include displaying the first image data, the second image data, and the object modeling data that are registered based on at least one selected from the point in time when the image is captured, the modality of the image, the posture of the scanned object, and the protocol.

The first image data may include at least one of a magnetic resonance imaging (MRI) image and a computed tomography (CT) image, and the second image data may include at least one of an x-ray image, an ultrasound image, and a position emission tomography (PET) image.

The preprocessing may be registering information included in the second image data and the object modeling data based on feature information which defines features shown in each of the multimodality images according to modality of medical images and the body tissues and biomedical information which defines information about external changes of the body tissues according to the modality of the images.

According to one or more embodiments of the present invention, there is provided a medical imaging apparatus including: an image processor including a processor which generates object modeling data based on information about shapes of body tissues of an object included in first image data, and revises the object modeling data based on information about shapes of body tissues of an object included in second image data, and an image viewer which displays the first image data, the second image data, and the revised object modeling data. The object modeling data is a virtual model embodying a body tissue structure of the object.

As at least one location is selected on the displayed object modeling data, the image viewer may display locations on the displayed first image data and second image data corresponding to at least one selected location.

The image viewer may display a marker on at least one location on the first image data and a marker on at least one location on the second image data. The markers on the at least one location on the first image data and the at least one location on the second image data may correspond to the at least one selected location.

The image processor may determine at least one area of a body tissue structure which is form among body tissue structures of the object modeling data and may correspond to the least one selected location. The image viewer may display an area on the displayed first image data and an area on the displayed second image data which correspond to the area of the at least one body tissue structure.

The image processor may generate diagnostic information necessary to diagnose a condition of a patient based on the object modeling data, and the image viewer may display the diagnostic information.

The object may include breast tissue, and the diagnostic information may include at least one of breast density, background parenchymal enhancement (BPE), degree of suspicion, and morpho-dynamic index (MDI).

The second image data may include an image, at least one of a point in time when an image is captured, modality of the image, a posture of a scanned object, and a protocol of the image by which the image is captured that is different from an image included in the first image data is captured.

The first image data may include at least one of a magnetic resonance imaging (MRI) image and a computed tomography (CT) image, and the second image data may include at least one of an X-ray image, an ultrasound image, a position emission tomography (PET) image.

The image processor may register information included in the second image data and the object modeling data based on feature information, which defines features of body tissues shown in the multimodal medical images based on modality of the multimodal medical images, and biomechanical information, which defines external changes to the body tissues according to the modality of multimodal medical images.

According to an aspect of an exemplary embodiment, there is provided a method of providing multimodal medical image information, the method including: loading first image data and second image data; registering the first image data and the second image data based on at least one of a point in time when an image is captured, modality of the image, a posture of a scanned object, and a protocol by which the image is captured; and displaying the first image data and the second image data.

The displaying the first image data and the second image data may include further displaying object modeling data that is generated based on at least one of the first image data and the second image data and is registered with the first image data and the second image data.

According to an aspect of an exemplary embodiment, there is provided a medical imaging apparatus including: an image processor which registers first image data and second image data based on at least one of a point in time when an image is captured, modality of the image, a posture of a scanned object, and a protocol by which the image is captured; and an image viewer which displays the first image data and the second image data.

The image viewer may further display object modeling data that is generated based on at least one of the first image data and the second image data and is registered with the first image data and the second image data.

According to an aspect of an exemplary embodiment, there is provided a computer-readable recording medium records a program thereon in order to execute the above-described methods in a computer.

According to an aspect of an exemplary embodiment, there is provided an apparatus for providing a medical image, the apparatus including: at least one memory operable to store program code; at least one processor operable to read the program code and operate as instructed by the program code, the program code causes the at least one processor to perform: obtaining a first image and a second image of an object according to a first modality and a second modality, respectively, the first modality being different from a second modality; generating a third image of the object based on at least one feature of the first image and the second image according to the first and second modalities; and displaying, on a display, the third image.

The at least one feature may include information which defines at least one of a brightness and a shape of an area of the object which corresponds to a tumor tissue.

BRIEF DESCRIPTION OF THE DRAWINGS

The above and/or other aspects will be more apparent by describing certain exemplary embodiments, with reference to the accompanying drawings, in which.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

As used herein, expressions such as "at least one of," when preceding a list of elements, modify the entire list of elements and do not modify the individual elements of the list.

Throughout the specification, when a portion is "connected" to another portion, the portion may be "directly connected" to the other portion, and also the portion may be "electrically connected" to the other portion by interposing a device therebetween. Also, when a portion "includes" an element, another element may be further included, rather than excluding the existence of the other element, unless otherwise described.

Breasts have soft tissues and are exposed to the outside. Thus, a shape of the breasts may significantly change due to gravity, pressure, or the like. Therefore, images of the breasts will be described as a main example of images of a scanned body portion of a patient in the exemplary embodiments. However, the exemplary embodiments are not limited thereto, and may be applied to medical images of other objects.

Figure 1:
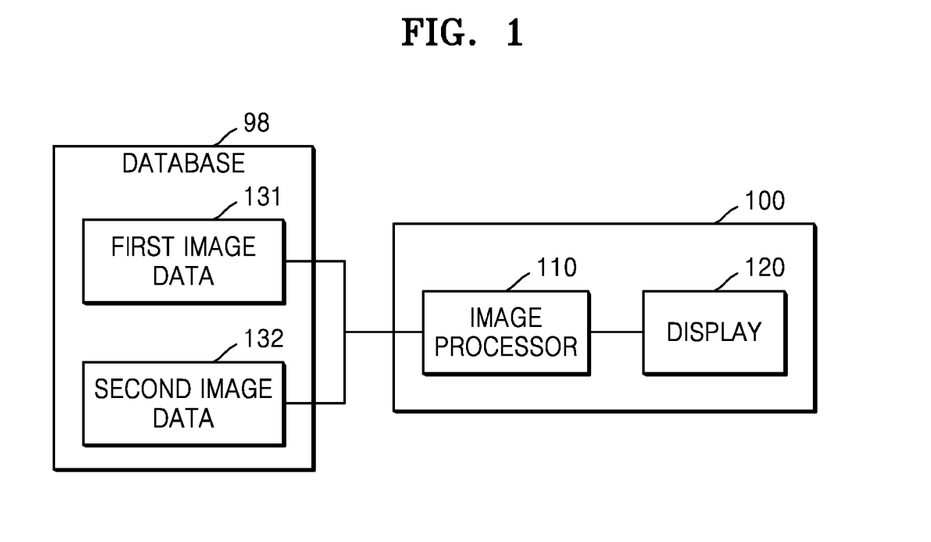
FIG. 1 is a block diagram illustrating a medical imaging apparatus according to an exemplary embodiment.

FIG. 1 is a block diagram illustrating a medical imaging apparatus 100 according to an exemplary embodiment. It should be noted that the medical imaging apparatus 100 shown in FIG. 1 is given as an example, and the medical imaging apparatus 100 according to an exemplary embodiment may have more or less components than those shown in FIG. 1. The medical imaging apparatus 100 may be a computer aided diagnostic apparatus, but is not limited thereto.

The medical imaging apparatus 100 may include an image processor 110 and a display 120. The image processor 110 may include at least one processor. For example, the at least one processor may include a central processing unit (CPU). Also, the image processor 110 may include a storage medium. The storage medium may be a computer readable recording medium such as a random access memory (RAM) or a read-only memory (ROM). The image processor 110 may generate object modeling data based on first image data 131.

The first image data 131 may include at least one first medical image of a body portion of a patient or data related to the at least one medical image. The first image data 131 may be a medical image acquired through medical imaging having higher sensitivity and may include a larger amount of information about body tissues. The first image data 131 may be, for example, a magnetic resonance (MR) image and/or a computed tomography (CT) image.

Figure 3:
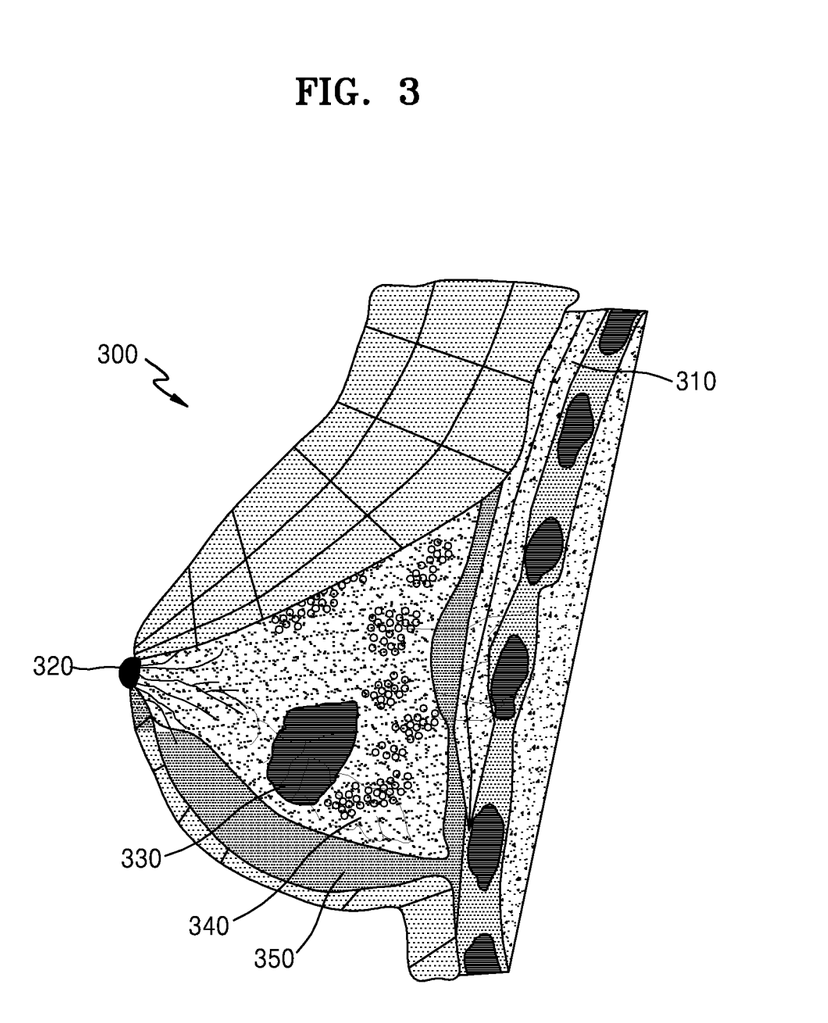
FIG. 3 is a view for explaining object modeling data according to an exemplary embodiment.

The object modeling data is information about a virtual model which models a body tissue structure based on the medical image. FIG. 3 shows an example of the object modeling data with regard to breast tissues 300. Referring to FIG. 3, the object modeling data of the breast tissues 300 may be configured as a model in which pectoral muscles 310, a nipple 320, a tumor tissue 330, glandular tissues 340, fat tissues 350, or the like are represented in a distinguishable manner. According to an exemplary embodiment, the object modeling data may be two-dimensional (2D) data or three-dimensional (3D) data. The object modeling data may vary according to an object included in the medical image.

Also, the image processor 110 may perform preprocessing to fuse second image data 132 with the object modeling data. In an exemplary embodiment, the second image data 132 is registered with the object modeling data, and based on the second image data 132 that is registered with the object modeling data, the object modeling data may be revised.

The second image data 132 may be at least one second medical image of a body portion acquired by medical imaging modality different from that used for acquiring the first image data 131. The second image data 132 may be a medical image acquired through medical imaging having higher specificity of body tissues than that of the first medical image. The second image data may be, for example, an ultrasound image, a 3D ultrasound image, and/or a position emission tomography (PET) image.

According to an exemplary embodiment, the first image data 131 and the second image data 132 may be data that includes medical images showing the same body portions. For example, in a case where the medical imaging apparatus 100 provides information about an image of a patient's brain, the first image data 131 may be an MR image of the patient's brain, and the second image data 132 may be at least one of a 2D ultrasound image and a 3D ultrasound image of the patient's brain. In addition, in a case where the medical imaging apparatus 100 provides information about a medical image of a heart, a carotid artery or a pelvis of a patient, the first image data 131 may be an MR image of the heart, the carotid artery or the pelvis of the patient, and the second image data 132 may be a 3D ultrasound image of the heart, the carotid artery or the pelvis of a patient. Also, in a case where the medical imaging apparatus 100 provides information about an image of a patient's prostate, the first image data 131 may be an MR image of the patient's prostate, and the second image data 132 may be an ultrasound image of the patient's prostate. In a case where the medical imaging apparatus 100 provides information about a liver image of a patient, the first image data 131 may be at least one of an MR image, a CT image and a PET-CT image of the patient's liver, and the second image data 132 may be at least one of a 2D ultrasound image and a 3D ultrasound image of the patient's liver. Furthermore, in a case where the medical imaging apparatus 100 provides information about a breast image of a patient, the first image data 131 may be at least one of an MR image and a CT image of the patient's breast, and the second image data 132 may be at least one of an ultrasound image and a mammographic image of the patient's breast. However, the above examples are given only for illustrative purposes, and the exemplary embodiments are not limited thereto.

According to an exemplary embodiment, the display 120 may substantially simultaneously display the first image data 131, the second image data 132, and the object modeling data. The display 120 may include a display device for displaying images. The display device may be a device which may display data on a screen thereof, and examples of the display device may include a liquid crystal display (LCD), a plasma display panel (PDP), a cathode ray tube (CRT), a light-emitting diode display, or an electro chromic display (ECD), but are not limited thereto.

Figure 4:
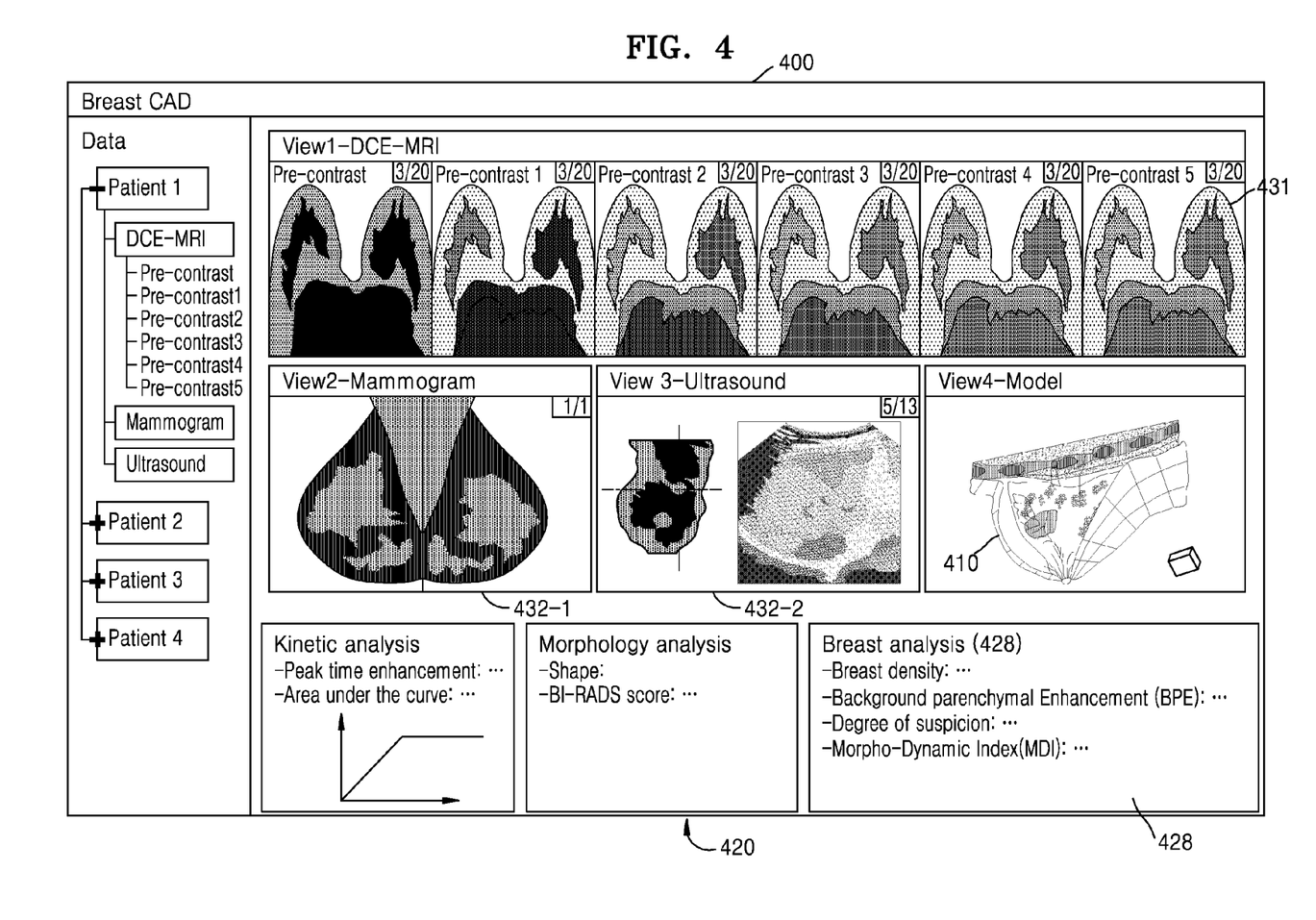
FIGS. 4, 5, and 6 are views illustrating example multi-modality images, according to an exemplary embodiment.

According to an exemplary embodiment, the display 120 may output a user interface (UI) 400 as illustrated in FIG. 4. FIG. 4 is a conceptual view of a multimodality image that is displayed according to an exemplary embodiment. Referring to FIG. 4, the display 120 may display an MR image or images 431 included in the first image data 131. Also, the display 120 may substantially simultaneously display a mammographic image 432-1 and an ultrasound image 432-2 included in the second image data 132. In addition, the display 120 may display object modeling data 410 that is generated based on the first and second image data 131 and 132.

When any one of the MR image 431, the mammographic image 432-1, the ultrasound image 432-2, and the object modeling data 410, which are illustrated in FIG. 4, receives a user input (e.g., scrolling), the display 120 may display another image corresponding to the user input.

According to an exemplary embodiment, the display 120 may also display information indicating a volume, a shape, and a length of the tumor tissue 330 included in the object modeling data 410.

According to an exemplary embodiment, the display 120 may display the object modeling data 410 together with a fusion image fused with one of the MR images 431, the mammographic image 432-1, and the ultrasound image 432-2.

The display 120 may generate diagnostic information 420 about body tissues of an object based on the object modeling data 410. The diagnostic information 420 may be information used for a user's diagnoses regarding the body tissues. For example, the diagnostic information 420 may include information with regard to biomarkers such as a breast density and background parenchymal enhancement (BPE), a degree of suspicion, and a morpho-dynamic index (MDI).

The image processor 110 may register information, which is included in the first image data 131 and the second image data 132, and generate the object modeling data 410 based on feature information and biomechanical information. The feature information may be information which defines features that are shown in images corresponding to the first image data 131 and the second image data 132 according to a modality thereof to generate phantom-based linear finite element modeling data. For example, the feature information may include information which defines brightness and a shape of areas which correspond to tumor tissues and are indicated on the MR image 431, in addition to contrast between the areas. The phantom-based linear finite element modeling data is data in which predetermined phantoms with regard to the object are linearly changed according to finite elements. The biomechanical information is information which defines information about shapes of body tissues that are non-linearly changed due to gravity and pressure to generate non-linear finite element modeling data based on biomechanics. In the case of a mammogram, pressure is applied to the breast tissues 300 while the breast tissues 300 are scanned. Also, when the breast tissues 300 are scanned by an MRI method, the patient lies supine and the breast tissues 300 of the patient are scanned. In addition, when the breast tissues 300 are scanned by an ultrasound method, the patient lies supine and the breast tissues 300 of the patient are scanned. In this case, since the breast tissues 300 include soft tissues, shapes thereof are non-linearly changed according to gravity and/or pressure. The biomechanical information may include information with regard to the shape of the breast tissues 300 that are non-linearly changed as shown in the MR image 431, the mammographic image 432-1, and the ultrasound image 432-2.

The display 120 may substantially simultaneously display kinetic analysis information and morphology analysis information about multimodality images. The kinetic analysis information may include information about peak time enhancement or an area of a region disposed under a curve, etc. The morphology analysis information may include information about shapes of tissues, breast imaging-reporting and data system (BI-RADS) scores, etc., which are morphological analysis results obtained based on the virtual model included in the object modeling data 410.

The image processor 110 may register the first image data 131 and the second image data 132 displayed through the display 120. In this case, the image processor 110 may register the first image data 131 and the second image data 132 based on at least one of a point in time when a multimodality image is captured, a modality of the image, a posture of the scanned object when the image is captured, and a protocol by which the image is captured. The first image data 131 and the second image data 132 registered by the image processor 110 may be displayed through the display 120. The display 120 may display the first image data 131, the second image data 132, and the object modeling data 410. Since the first image data 131, the second image data 132, and the object modeling data 410 are registered with one another, when any one of the first image data 131, the second image data 132, and the object modeling data 410 receives a user input (e.g., scrolling) such that the view thereof is changed, views of the remaining two from among the first image data 131, the second image data 132, and the object modeling data 410 may be changed based on the registered information. Also, when a location of a first marker is set for any one of the first image data 131, the second image data 132, and the object modeling data 410, second and third markers may also be displayed at locations of the remaining two from among the first image data 131, the second image data 132, and the object modeling data 410, to correspond to the set location of the first marker.

Figure 2:
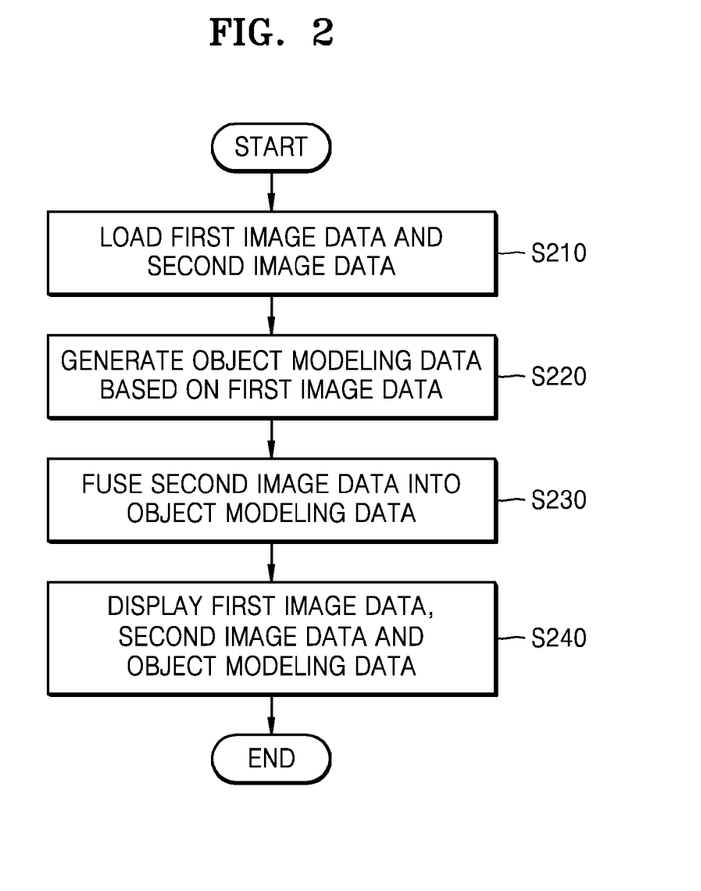
FIG. 2 is a flowchart illustrating a method of providing medical images according to an exemplary embodiment.

FIG. 2 is a flowchart illustrating a method of providing medical images according to an exemplary embodiment.

In operation 210, the image processor 110 of the medical imaging apparatus 100 may load the first image data 131 and the second data 132 from a database 98 stored in a memory. Alternatively, the image processor 110 may receive at least one of the first image data 131 and the second image data 132 from a corresponding imaging modality in real time. Here, the second image data 132 may include an image and information about at least one of a point in time when the image is captured, a modality of the image, a posture of the scanned object when the image is captured, and a protocol of the image. The protocol of the image of the second image data 132 may be different from that of the first image data 131. For example, the first image data 131 may include an MR image and/or a CT image, and the second image data 132 may include an ultrasound image, an X-ray image, and/or a PET image.

Next, based on the first image data 131, the image processor 110 may generate the object modeling data 410 in operation S220. The image processor 110 performs image processing related to the first image data 131, and may classify images included in the first image data 131 according to body tissues. The image processor 110 may determine a structure and a shape of the virtual model included in the object modeling data 410 according to shapes of the body tissues.

In operation S220, the image processor 110 may analyze the first image data 131 based on the feature information and the biomechanical information corresponding to modality of the first image data 131. According to a result of the analysis, the image processor 110 may generate the object modeling data 410.

Next, in operation S230, the image processor 110 of the medical imaging apparatus 100 may perform preprocessing to fuse the second image data 132 with the object modeling data 410 generated in operation S220. That is, the image processor 110 may revise the object modeling data 410 based on the second image data 132.

A shape of the object included in the second image data 132 may be different from that of the object included in the first image data 131. The second image data 132 is registered with the object modeling data 410 to combine the information included in the second image data 132 with the object modeling data 410. According to an exemplary embodiment, the image processor 110 may register the information included in the second image data 132 and the object modeling data 410 based on the feature information and the biomechanical information in accordance with modality of the second image data 132.

For convenience of explanation, operations S220 and S230 are described as separate operations in an exemplary embodiment of FIG. 2. However, the image processor 110 may generate the object modeling data 410 based on the information included in the first image data 131 and the second image data 132 in one operation.

In operation S240, the display 120 may display the first image data 131, the second image data 132, and the object modeling data 410, which is revised in operation S230. As illustrated in FIG. 4, the display 120 may substantially simultaneously display the first image data 131, the second image data 132, and the object modeling data 410, which is revised in operation S230. The first image data 131, the second image data 132, and the object modeling data 410 may be images that are registered with one another by the image processor 110.

As shown in FIG. 4, the image processor 110 may generate the diagnostic information 420 for diagnosing a condition of a patient based on the object modeling data 132. The diagnostic information 420 may include information about, for example, major axes, minor axes, volume, etc. of body tissues included in the object modeling data 410. Also, when the object of images, which are included in the first image data 131 and the second image data 132, is, for example, a breast tissue, the diagnostic information 420 may include additional information 428 of at least one of, for example, breast density information, BPE information, degree of suspicion, and MDI information. For example, such information may be provided for all of the patients or for high-risk patients only.

The medical imaging apparatus 100 may further include an input device (not shown). The medical imaging apparatus 100 may receive an input for selecting at least one location on the virtual model included in the object modeling data 410 through the input device. When the at least one location is selected, the display 120 may display locations on the first image data 131 and the second image data 132 corresponding to the least one selected location.

When the first image data 131 and the second image data 132 are processed, the medical imaging apparatus 100 may register the first image data 131 and the second image data 132 based on at least one of a point in time when an image included in the first image data 131 or the second image data 132 is captured, modality of the image, a posture of the scanned object when the image is captured, and a protocol by which the image is captured. Also, the medical imaging apparatus 100 may display the registered first image data 131 and second image data 132. Also, the medical imaging apparatus 100 may register the first image data 131, the second image data 132, and the object modeling data 410 with one another.

Figure 5:
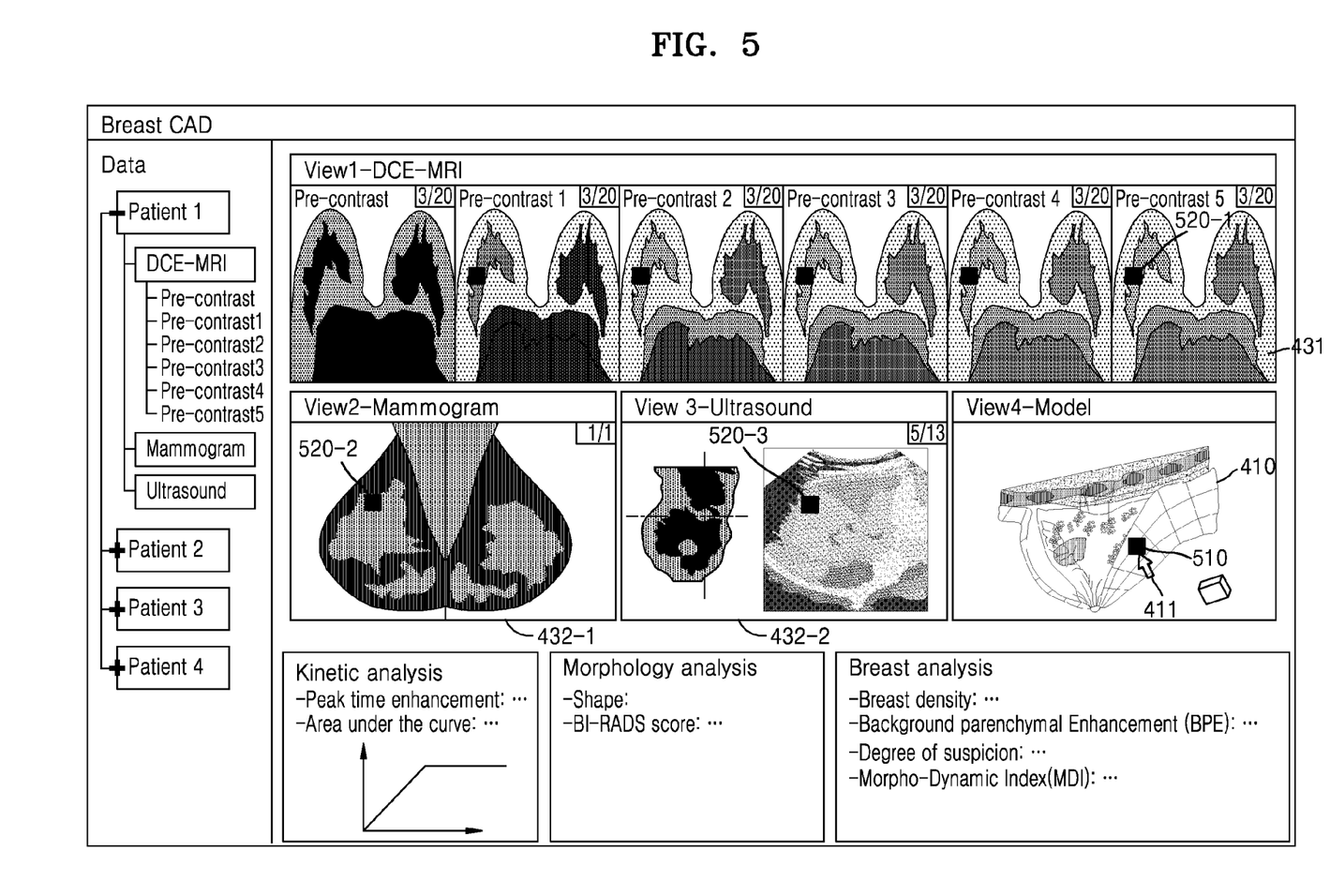

FIG. 5 is a conceptual view showing registration points indicated on each of multimodality images and displayed, according to an exemplary embodiment.

The medical imaging apparatus 100 may receive an input for selecting a location 510 on the virtual model, which is included in the object modeling data, through the input device, i.e., by placing a cursor (pointer 411) on the image 410. The image processor 110 of the medical imaging apparatus 100 may determine locations 520-1 on the first image data and locations 520-2, 520-3 on the second image data corresponding to the selected location 510.

Figure 6:
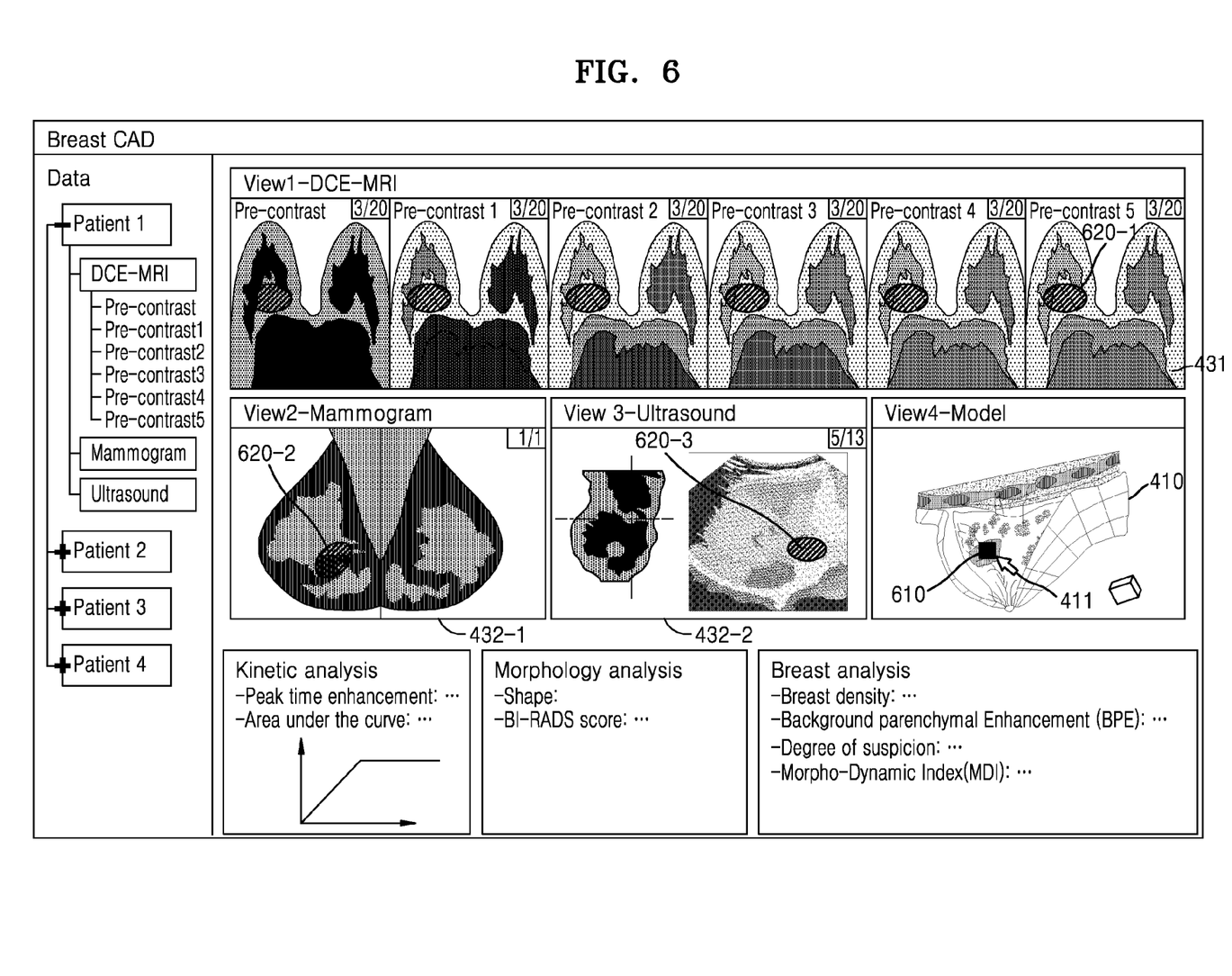

FIG. 6 is a conceptual view of a screen on which registration points of multimodality images are displayed according to an exemplary embodiment.

The medical imaging apparatus 100 may receive an input for selecting a location 610 on the virtual model included in the object modeling data through the input device. The image processor 110 of the medical imaging apparatus 100 may determine shapes of body tissues included in the object modeling data, which correspond to the selected location 610. For example, when a user selects tumor tissues included in the object modeling data by using a pointer 411, the image processor 110 may select the tumor tissues. Next, the image processor 110 may determine which areas on the first image data, i.e., images 431 correspond to the selected tumor tissues. In addition, the image processor 110 may determine which areas on the second image data, i.e., images 432-1 and 432-2, correspond to the selected tumor tissues.

The display 120 of the medical imaging apparatus 100 may display areas 620-1, 620-2 and 620-3 determined by the image processor 110. According to an exemplary embodiment, the display 120 may use a single color to display the determined areas 620-1, 620-2 and 620-3. According to an exemplary embodiment, the display 120 may display edges of the determined areas 620-1, 620-2 and 620-3 as closed curves.

In addition, exemplary embodiments may also be implemented through computer readable code and/or instructions on a medium, e.g., a computer readable medium, to control at least one processing element to implement any of the above described exemplary embodiments. The medium may correspond to any medium or media which serve as a storage and/or perform transmission of the computer readable code.

The computer readable code may be recorded and/or transferred on a medium in a variety of ways, with examples of the medium including recording media, such as magnetic storage media (e.g., ROM, floppy disks, hard disks, etc.) and optical recording media (e.g., compact disc read only memories (CD-ROMs), or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of providing multimodal medical images, the method comprising:

loading first image data and second image data obtained by two different imaging modalities;

generating object modeling data based on at least one among the first image data and the second image data;

displaying, on a display, the first image data, the second image data and the object modeling data that are registered based on information about a posture of an object during imaging of at least one among the first image data and the second image data;

based on receiving an input of selecting a location on the displayed object modeling data, determining locations on the displayed first image data and the displayed second image data which correspond to the selected location; and displaying the determined locations on the first image data and the second image data, respectively.

2. The method of claim 1, wherein the displaying the determined locations comprises displaying a marker on each of the determined locations.

3. The method of claim 1, wherein the determining the locations comprises:

determining an area of the object modeling data corresponding to the selected location; and determining a first area on the displayed first image data and a second area on the displayed second image data which correspond to the determined area of the object modeling data, wherein the displaying comprises displaying the first area and the second area on the first image data and the second image data, respectively.

4. The method of claim 1, further comprising generating diagnostic information for diagnosing a condition of the object based on the object modeling data, wherein the displaying the first image data, the second image data, and the object modeling data comprises further displaying the diagnostic information.

5. The method of claim 4, wherein the diagnostic information comprises at least one among a breast density, background parenchymal enhancement (BPE), a degree of suspicion, and a morpho-dynamic index (MDI), of a breast tissue.

6. The method of claim 1, wherein the second image data comprises a second image and information about at least one among a point in time when the second image is captured, an identification of an imaging modality of the second image, the posture of the object during imaging of the second image data, and a second protocol by which the second image is captured, the second protocol being different from a first protocol by which a first image included in the first image data is captured.

7. The method of claim 1, wherein the displaying the first image data, the second image data, and the object modeling data comprises:

displaying the first image data, the second image data, and the object modeling data that are registered further based on at least one among a point in time when the first image data or the second image data is captured, an imaging modality of the first image data or the second image data, and the first or second protocol by which the first image data or the second image data is captured.

8. The method of claim 1, wherein the first image data comprises at least one among a magnetic resonance (MR) image and a computed tomography (CT) image, and the second image data comprises at least one among an X-ray image, an ultrasound image, and a position emission tomography (PET) image.

9. The method of claim 1, wherein the generating the object modeling data comprises:

generating the object modeling data based on the first image data; and revising the object modeling data based on the second image data.

10. The method of claim 9, wherein the revising the object modeling data comprises revising the object modeling data based on at least one among feature information which defines a feature of a body tissue of the object based on an imaging modality of the second image data, and biomechanical information which defines information about a change in shape of the body tissue according to the imaging modality corresponding to the second image data.

11. A non-transitory computer-readable recording medium having recorded thereon a program, which, when executed by a computer, causes the computer to execute the method of claim 1.

12. The method of claim 1, wherein the first image data, the second image data and the object modeling data are displayed on the display together.

13. A medical imaging apparatus comprising:

a display; and a processor configured to:

generate object modeling data based on at least one among first image data and second image data obtained by different imaging modalities;

control the display to display the first image data, the second image data, and the object modeling data that are registered based on information about a posture of an object during imaging of at least one among the first image data and the second image data;

based on receiving an input of selecting a location on the displayed object modeling data, determine locations on the displayed first image data and the displayed second image data which correspond to the selected location; and control the display to display the determined locations on the first image data and the second image data, respectively.

14. The medical imaging apparatus of claim 13, wherein the processor is configured to control the display to display markers on the determined locations.

15. The medical imaging apparatus of claim 13, wherein the processor is configured to determine an area of the object modeling data corresponding to the selected location, determine a first area on the first image data and a second area on the second image data that correspond to the determined area of the object modeling data, and control the display to display the first area and the second area on the first image data and the second image data, respectively.

16. The medical imaging apparatus of claim 13, wherein the processor is configured to generate diagnostic information for diagnosing a condition of the object based on the object modeling data, and wherein the processor is configured to control the display to display the diagnostic information.

17. The medical imaging apparatus of claim 16, wherein the diagnostic information comprises at least one among a breast density, background parenchymal enhancement (BPE), a degree of suspicion, and a morpho-dynamic index (MDI), of a breast tissue.

18. The medical imaging apparatus of claim 12, wherein the first image data and the second image data comprise a first image and a second image, respectively, the processor is configured to register the first image data, the second image data, and the object modeling data further based on at least one among a point in time when the first image or the second image is captured, an imaging modality of the first image or the second image, and a protocol by which the first image or the second image is captured.

19. The medical imaging apparatus of claim 12, wherein the second image data comprises a second image and information about at least one among a point in time when the second image is captured, an identification of an imaging modality of the second image, the posture of the object during imaging, and a second protocol by which the second image is captured, the second protocol being different from a first protocol by which a first image included in the first image data is captured.

20. The medical imaging apparatus of claim 12, wherein the first image data comprises at least one among a magnetic resonance (MR) image and a computed tomography (CT) image, and
the second image data comprises at least one among an X-ray image, an ultrasound image, and a position emission tomography (PET) image.

21. The medical imaging apparatus of claim 12, wherein the processor is configured to generate the object modeling data based on the first image data and revise the object modeling data based on the second image data.

22. The medical imaging apparatus of claim 21, wherein the processor is configured to register information included in the second image data and the object modeling data based on at least one among feature information, which defines a feature of a body tissue of the object based on an imaging modality of the second image data, and biomechanical information, which defines an external change to the body tissue according to the imaging modality corresponding to the second image data.

23. The medical imaging apparatus of claim 13, wherein the first image data, the second image data and the object modeling data are displayed on the display together.

24. The medical imaging apparatus of claim 13, wherein the processor is further configured to control the display to display a third image data registered with the object modeling data.

25. A method of providing multimodal medical image information, the method comprising:
loading first image data and second image data, the first image data and the second image data comprising a first image and a second image, respectively, obtained by different imaging modalities;
registering the first image data and the second image data with object modeling data based on information about a posture of an object during imaging of at least one among the first image data and the second image data;
displaying the first image data, the second image data, and the object modeling data on a display;
based on receiving an input of selecting a location on the displayed object modeling data, determining locations on the displayed first image data and the displayed second image data which correspond to the selected location; and
displaying the determined locations on the first image data and the second image data, respectively.

26. The method of claim 25, wherein the object modeling data is generated based on at least one among the first image data and the second image data and is registered with the first image data and the second image data.

27. A non-transitory computer-readable recording medium having recorded thereon a program, which, when executed by a computer, causes the computer to execute the method of claim 25.

28. A medical imaging apparatus comprising:
a display; and
a processor configured to:
register first image data and second image data respectively comprising a first image and a second image with object modeling data based on information about a posture of an object during imaging of at least one among the first image data and the second image data;
control the display to display the first image data, the second image data, and the object modeling data;
based on receiving an input of selecting a location on the displayed object modeling data, determine locations on the displayed first image data and the displayed second image data which correspond to the selected location; and
control the display to display the determined locations on the first image data and the second image data, respectively.

29. The medical imaging apparatus of claim 28, wherein the object modeling data is generated based on at least one among the first image data and the second image data and is registered with the first image data and the second image data.

* * * * *